United States Patent [19]

Magnussen et al.

[11] 4,360,695

[45] Nov. 23, 1982

[54] CONTINUOUS PREPARATION OF ADIPTIC ACID

[75] Inventors: Peter Magnussen, Bad Durkheim; Volker Schumacher, Frankenthal; Wolfgang Gebert, Wesseling; Heinrich Reitz, Mannheim; Werner Praetorius, Ludwigshafen, all of Fed. Rep. of Germany

[73] Assignee: BASF Aktiengesellschaft, Fed. Rep. of Germany

[21] Appl. No.: 337,684

[22] Filed: Jan. 7, 1982

[51] Int. Cl.$^3$ .......................... B01D 3/14; C07C 54/14
[52] U.S. Cl. ...................................... 562/590; 203/28; 203/41; 203/93; 203/DIG. 19; 562/593
[58] Field of Search .................. 562/593, 590; 203/41, 203/28, DIG. 19, 98; 202/664, 669; 210/664, 669

[56] References Cited

U.S. PATENT DOCUMENTS 3,551,300  12/1970  Congley ............................... 203/41

FOREIGN PATENT DOCUMENTS

| 1602512 | 1/1971 | France. | |
|---|---|---|---|
| 46-27166 | 8/1971 | Japan | 260/593 |
| 47-38416 | 9/1972 | Japan | 260/593 |
| 1516665 | of 0000 | Japan. | |

*Primary Examiner*—Frank Sever
*Attorney, Agent, or Firm*—Keil & Witherspoon

[57] ABSTRACT

In a process for the continuous preparation of adipic acid by hydrolysis of $C_1$-$C_4$-alkyl adipates with water at an elevated temperature in the presence of a strongly acidic ion exchanger, the improvement that the esters and excess water are fed to the middle section of a column, reaction mixture is taken off at a plurality of trays of the column below the feed point, passed over a strongly acidic ion exchanger and recycled, alkanols or alkanol/water mixtures are taken off at the top of the column and an aqueous solution of adipic acid is taken off at the bottom of the column.

5 Claims, No Drawings

CONTINUOUS PREPARATION OF ADIPTIC ACID

The present invention relates to a process for the continuous preparation of adipic acid by hydrolyzing $C_1$–$C_4$-alkyl adipates with water at an elevated temperature in the presence of a strongly acidic ion exchanger.

Japanese Published Patent Application No. 15,166/65 discloses that adipic acid is obtained by hydrolyzing dimethyl adipate with excess water in the absence of a catalyst at 175° C. This process has the disadvantage that because of the high temperatures required by-products are formed, which are difficult to separate off. Further, French Pat. No. 1,602,512 mentions that the hydrolysis of esters with mineral acids has disadvantages since technically complicated corrosion-resistant apparatus is required. It also states that hydrolysis with alkaline agents causes discoloration and degradation of the desired acid. Furthermore, the same patent discloses that 2-oxopentanedicarboxylic acid ethyl ester can be hydrolyzed in a mixture of alcohol and water, in the presence of a strongly acidic ion exchanger, at an elevated temperature, to give the corresponding acid. The process has the disadvantage that it requires a residence time of 4–5 hours. Furthermore, the procedure described is unsuitable for continuous industrial operation.

It is an object of the present invention to provide a method of hydrolyzing adipic acid esters to adipic acid wherein no decomposition of the adipic acid takes place and the reaction can be carried out continuously in a simple manner, without abrasion of the ion exchanger employed.

We have found that this object is achieved by a process for the continuous preparation of adipic acid by hydrolysis of $C_1$–$C_4$-alkyl adipates with water at an elevated temperature in the presence of a strongly acidic ion exchanger, wherein the esters and excess water are fed to the middle section of a column, reaction mixture is taken off at a plurality of trays of the column below the feed point, passed over a strongly acidic ion exchanger and recycled, alkanols or alkanol/water mixtures are taken off at the top of the column and an aqueous solution of adipic acid is taken off at the bottom of the column.

The novel process has the advantage that it is simple to operate as a continuous industrial process and that the ion exchanger can be replaced without interrupting the operation. Further, the novel process has the advantage that no decomposition of the adipic acid occurs. Finally, it has the advantage that it takes place with a shorter residence time and that there is no danger of abrasion of the ion exchanger.

The starting materials used are $C_1$–$C_4$-alkyl adipates. Examples of suitable esters are dimethyl adipate, diethyl adipate, dipropyl adipate and dibutyl adipate, amongst which dimethyl adipate is industrially of particular importance.

The hydrolysis is carried out with excess water, ie. more than 2 moles of water per mole of adipic acid ester. The amount of water depends on the desired concentration of the adipic acid solution to be prepared. Advantageously, from 3.5 to 40, especially from 15 to 25, moles of water are employed per mole of adipic acid ester.

The adipic acid ester and water are advantageously fed as a mixture to the middle section of a column. The column used advantageously has liquid standing on each of the trays, at least below the feed point. Examples of suitable columns are bubble-cap tray columns and valve-tray columns. The column advantageously has 10–35 trays below the feed point of the adipic acid ester and water and 15–20 trays above the feed point. Column designs suitable for separating mixtures of alkanols, water and ester may be used for the rectifying section above the feed point. Advantageously, reaction mixture is taken off every tray of the column below the feed point of the mixture of adipic acid ester and water. The reaction mixture essentially consists of adipic acid ester, water, adipic acid and alkanol. The mixture is passed over a strongly acidic ion exchanger and is recycled to the column, advantageously to the same tray as that from which it was taken, or to one or two trays above this, the first-mentioned embodiment having proved particularly suitable. Another suitable method has proved to be to take reaction mixture only off every third to fifth tray of the column and pass it over the strongly acidic ion exchanger. Preferably, the amount passed over the strongly acidic ion exchanger from each take-off point is from 5 to 30, especially from 15 to 20, times as great as the throughput of the column.

Accordingly, adipic acid ester is progressively hydrolyzed below the feed point of the adipic acid ester and water, and the alkanols resulting from the hydrolysis distil and are separated off above the feed point. Accordingly, the particular alkanols split off, or their mixtures with water, are taken off at the top of the column and an aqueous solution of adipic acid, for example of from 20 to 85% strength by weight, is taken off at the bottom of the column.

Advantageously, the temperature in the column section below the feed point is kept at from 80° to 130° C., especially from 90° to 120° C. These temperatures also apply to the recycled reaction mixture. Of course, the temperature also depends on the boiling point of the alkanol to be split off; this is also true of the rectifying section of the column, above the feed point.

Examples of suitable strongly acidic ion exchangers are crosslinked polystyrenes having acidic groups, in particular sulfonic acid groups. Styrene/divinylbenzene copolymers having sulfonic acid groups have proved particularly suitable. Other strongly acidic and water-insoluble solids, such as zeolites, can also be used. Advantageously, from 0.1 to 10 liters of strongly acidic ion exchanger are used per liter of reaction mixture per hour in each of the individual circuits. The lower the amount of exchanger employed, the higher is the consumption of steam for a given desired conversion to adipic acid.

An advantageous method of isolating adipic acid from the aqueous adipic acid solution taken off at the bottom of the column is crystallization, for example under reduced pressure. The mother liquor thus obtained, which contains, for example, from 2 to 6% by weight of adipic acid and impurities, is advantageously recycled, ie. returned to the column together with fresh adipic acid ester. Of course, the shortfall in the amount of water is correspondingly made up. Before reuse, the mother liquor resulting from the crystallization is suitably treated, for example by extraction with adipic acid ester or, in particular, by passing over active charcoal.

The adipic acid prepared according to the invention is useful for the preparation of hexamethylenediammonium adipate.

The Examples which follow illustrate the process according to the invention.

COMPARATIVE EXAMPLE 350 g of dimethyl adipate and 700 g of water were reacted in a stirred autoclave through which nitrogen was passed. The amount of nitrogen was adjusted so that about 100 g/h of water/methanol mixture were discharged under the prevailing pressure. Whilst, if the reaction mixture was at 182° C., the conversion to adipic acid after 1.5 h was only 22%, the corresponding conversion was 75% at 227° C. However, the product obtained at 227° C. showed a distinct yellow discoloration.

The addition of 10% of zeolite gave 42% conversion to adipic acid after 1.5 h at 180° C.

EXAMPLE 1

The hydrolysis of dimethyl adipate was carried out in an 80 cm bubble-cap tray column with 10 trays. Per hour, 150 g of dimethyl adipate and 300 g of water were fed to the first tray. 21 g/h of reaction mixture were taken from each of the ten trays in the stripping section below the feed point, passed over a fixed bed containing 50 ml of ion exchanger (consisting of crosslinked polystyrene having sulfonic acid groups) and recycled to the same tray. The reaction was carried out under atmospheric pressure at 95°–105° C. In the bottom of the column, an aqueous solution containing 31% by weight of adipic acid and 1% by weight of monomethyl adipate was obtained, whilst 69 ml of methanol per hour were taken off at the top of the column. The material discharged from the bottom was pumped into a cooled crystallizer. The adipic acid was separated from the mother liquor on a belt filter and the mother liquor was topped up with water and recycled to the reaction column.

EXAMPLE 2

The hydrolysis of dimethyl adipate was carried out in an industrial reaction column consisting of a bubble-cap tray column with 30 trays, surmounted by a packed column. 12 kg/h of dimethyl adipate and 26 kg/h of water or mother liquor were fed to the first tray of the bubble-cap tray column. 600 kg/h of reaction mixture were taken from every third tray of the 30 trays in the stripping section, and each of these streams was pumped over a fixed bed of acidic ion exchanger (crosslinked polystyrene having sulfonic acid groups) and recycled to the same tray as that from which it was taken.

The aqueous adipic acid solution in the bottom contained only 0.1% by weight of monomethyl adipate and no dimethyl adipate. The material discharged from the bottom was passed into a vacuum crystallizer, and the adipic acid was subsequently separated from the mother liquor in a centrifuge. The mother liquor, which still contained 5.5% by weight of adipic acid, was topped up with water and recycled to the reaction column.

EXAMPLE 3

The mother liquor from Example 1 was extracted, in a mixer-separator, with dimethyl adipate in a volume ratio of 10:1, at 40° C. The UV number of the mother liquor, which is a measure of the concentration of impurities in the mother liquor, was thereby reduced by 50%.

EXAMPLE 4

The mother liquor from Example 1 was passed, at 30° C., over a fixed bed containing 50 g of ash-free active charcoal. This reduced the UV number of the mother liquor by 40%.

We claim:

1. In a process for the continuous preparation of adipic acid by hydrolysis of $C_1$–$C_4$-alkyl adipates with water at an elevated temperature in the presence of a strongly acidic ion exchanger, the improvement that the esters and excess water are fed to the middle section of a column, reaction mixture is taken off at a plurality of trays of the column below the feed point, passed over a strongly acidic ion exchanger and recycled, alkanols or alkanol/water mixtures are taken off at the top of the column and an aqueous solution of adipic acid is taken off at the bottom of the column.

2. A process as claimed in claim 1, wherein from 3.5 to 40 moles of water are employed per mole of adipic acid ester.

3. A process as claimed in claim 1, wherein the temperature in the column, below the feed point of adipic acid ester and water, is kept at from 80° to 130° C.

4. A process as claimed in claim 1, wherein reaction mixture is taken off every 3rd to 5th tray below the feed point of adipic acid ester and water and is passed over the strongly acidic ion exchanger.

5. A process as claimed in claim 1, wherein each stream of reaction mixture taken off is recycled to the same tray in the column.

* * * * *

UNITED STATES PATENT AND TRADEMARK OFFICE
CERTIFICATE OF CORRECTION

PATENT NO.    : 4,360,695

DATED         : November 23, 1982

INVENTOR(S)   : Peter MAGNUSSEN et al.

It is certified that error appears in the above—identified patent and that said Letters Patent is hereby corrected as shown below:

On the title page, following the section labelled "[22]" insert the Claim to Priority data in the application.

-- [30] Foreign Application Priority Data

Jan. 21, 1981        Germany.....3101716  --.

Signed and Sealed this

Fifteenth Day of March 1983

[SEAL]

Attest:

GERALD J. MOSSINGHOFF

Attesting Officer    Commissioner of Patents and Trademarks